United States Patent [19]

Rossen

[11] Patent Number: 5,700,364
[45] Date of Patent: Dec. 23, 1997

[54] ELECTROCHEMICAL OXIDATION

[75] Inventor: Kai Rossen, Westfield, N.J.

[73] Assignee: Merck & Co., Inc., Rahway, N.J.

[21] Appl. No.: 742,430

[22] Filed: Oct. 30, 1996

Related U.S. Application Data

[60] Provisional application No. 60/008,125, Oct. 30, 1995.
[51] Int. Cl.$^6$ .................. C25B 3/00; C07D 263/52; C07D 263/60; C07D 413/00
[52] U.S. Cl. .................. 205/425; 205/436; 205/438; 205/456; 205/463; 548/217
[58] Field of Search .................. 205/425, 428, 205/436, 438, 456, 463; 548/217

[56] References Cited

U.S. PATENT DOCUMENTS 5,618,937  4/1997  Askin et al. .................. 544/360

OTHER PUBLICATIONS

J. Org. Chemistry, Torii et al., 1981, vol. 46, p. 3312 no month available.
Top. Curr. Chem., Torii, et al., 1988, vol. 148, p. 153 no month available.
Scott, et al., Chem. Eng. Res. Des., 1995, vol. 73 (A3), p. 330 no month available.

*Primary Examiner*—Kathryn L. Gorgos
*Assistant Examiner*—Edna Wong
*Attorney, Agent, or Firm*—Mary A. Appollina; Melvin Winokur; Jack L. Tribble

[57] ABSTRACT

A process for synthesizing the compounds wherein X is halo, consists of, at a minimum, electrochemical oxidation of the allyl acetonide reactant with halide salt in an aqueous system, the desired compounds being useful as intermediates for the synthesis of inhibitors of renin or HIV protease or other proteases.

14 Claims, No Drawings

ELECTROCHEMICAL OXIDATION

This application is related to provisional application Ser. No. 60/008,125 filed Oct. 30, 1995.

BACKGROUND OF THE INVENTION

The present application is related to Merck Cases 19182IA, 19045, 19046, 19046IA and U.S. Pat. Nos. 5,169,952 and 5,413,999.

The present invention is concerned with a novel intermediate and process for sythesizing compounds which inhibit the protease encoded by human immunodeficiency virus (HIV), and in particular, the compound disclosed and referred to as "Compound J" in U.S. Pat. No. 5,413,999.

Compound J

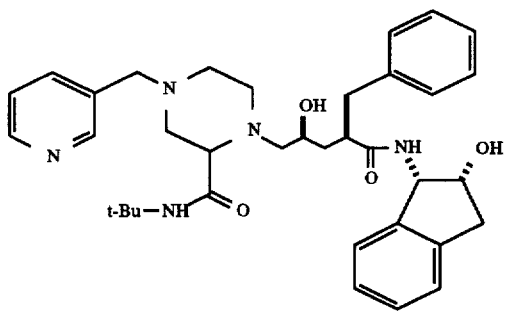

These compounds am of value in the prevention of infection by HIV, the treatment of infection by HIV and the treatment of the resulting acquired immune deficiency syndrome (AIDS).

More specifically, the instant process involves the preparation of the epoxide intermediate for the production of Compound J, the HIV protease inhibitor depicted above. The process relates to electrochemical epoxidation of allyl acetonide 2 in an electrochemical cell with halide salt in an aqueous system with a water miscible organic cosolvent.

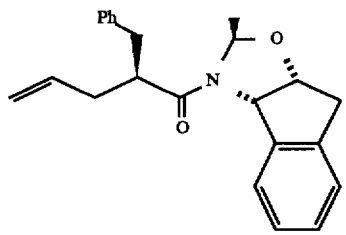

Allyl acetonide

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Rather, L. et al., *Nature*, 313, 277 (1985)]. Amino acid sequence hornology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including Compound J, that can be made from the novel intermediates and process of this invention are inhibitors of HIV protease, and are disclosed in EPO 541,168, which published on May 12, 1993.

Previously, the synthesis of Compound J and related compounds was accomplished via a 12-step procedure which employed a hydroxy protected dihydro-5(S)-hydroxymethyl-3(2H) furanone which was alkylated, and involved replacement of an alcohol leaving group on the alkylated furanone with a piperidine moiety. The coupled product was then hydrolyzed to open the furanone ting into a hydroxy acid moiety, and the acid was ultimately coupled to 2(R)-hydroxy-1(S)-aminoindane. This procedure is described in EPO 541,168. The extreme length of this route (12 steps), renders this process time consuming and labor intensive, and it requires the use of many expensive reagents and an expensive starting material. A route requiring fewer reaction steps and/or more efficient reagents would provide desirable economical and time-saving benefits.

The iodolactamization of olefinic tertiary amide A is known to occur with subsequent hydrolysis of the charged iodoiminolactam B intermediate giving the iodolactone C as the only isolated product (Scheme ALPHA). See Tamara, Y. et al., *J. Am. Chem. Soc.*, 106, 1079–1085 (1984); Trost, B. M. et al., eds. Comprehensive Organic Synthesis; Selectivity, Strategy, & Efficiency in Modern Organic Chemistry, Volume 4. Pergamon Press, New York 1991, p. 398–421. In this process, it is known that very efficient chirality transfer occurs from the 2-position to the 4-position, to give the 2,4-syn products (represented by the corresponding hydroxy-acid D) in high diastereoselectivity.

SCHEME ALPHA

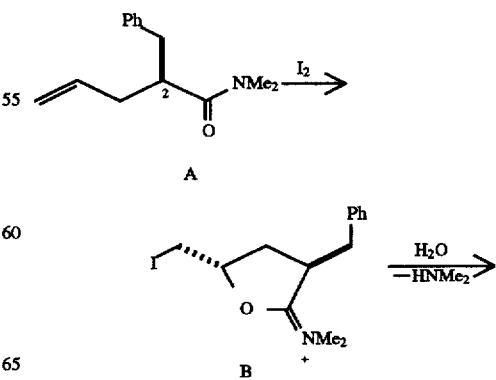

-continued
SCHEME ALPHA

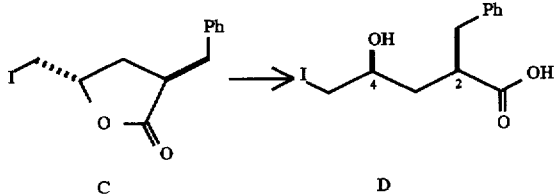

-continued
SCHEME BETA

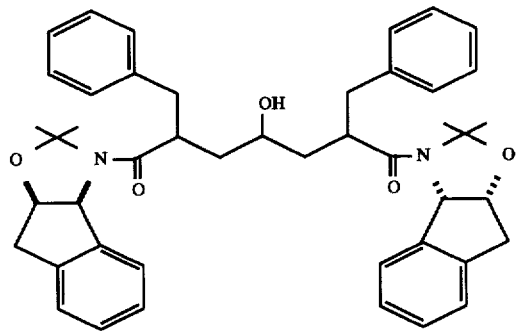

Double Addition Products

In another existing process, the acetonide is reacted with (S)-glycidyl tosylate in the presence of strong base LHMDS to form the epoxide (see Scheme BETA). Since both the starting material (S)-glycidyl tosylate and product are epoxides, the acetonide anion reacts also with the product epoxide; therefore, about 20% double addition byproducts after formed, in addition to the product epoxide in 71% yield. After crystallization from MeOH, an additional MTBE recrystallization was required to provide the epoxide free of dimer; consequently the overall isolated yield from the acetonide can range from 56–61%. The formation of double nucleophilic addition products is a problem inherent to the electrophile glycidyl tosylate. The (S)-glycidyl tosylate is also a very costly raw material in the synthesis of Compound J.

In another existing process, the epoxide is prepared by reacting allyl acetonide 2 with NCS and NaI to give iodohydrin, which is converted in a separate step to epoxide 3 with strong base. See, e.g., Maligres, P. E. et al., *Tetrahedron Lett.*, 36, 2195 (1995).

The present process is markedly different from these existing methods. In the present invention, epoxide 3 is prepared by the electrochemical oxidation of allyl acetonide 2 with bromide or iodide salt in an aqueous system with a water miscible organic cosolvent. In an alternative embodiment of the present invention, the halohydrin intermediate 3a

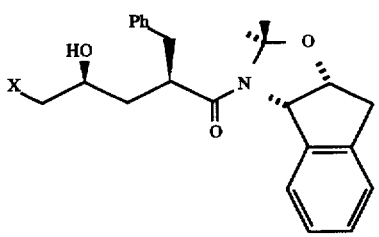

(X is halo);

is prepared by substituting the water miscible solvent with a water immiscible solvent, i.e., electrochemical oxidation of allyl acetonide 2 with bromide or iodide salt with a water immiscible solvent.

The present process is only one step and avoids expensive and environmentally hazardous reagents such as iodide.

SUMMARY OF THE INVENTION

A process is disclosed for synthesizing the epoxide of the formula

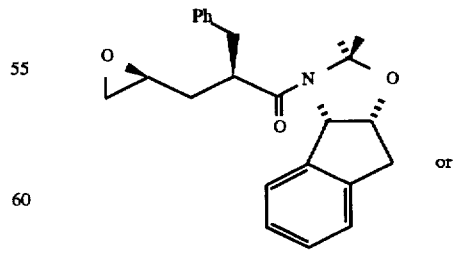

or

SCHEME BETA

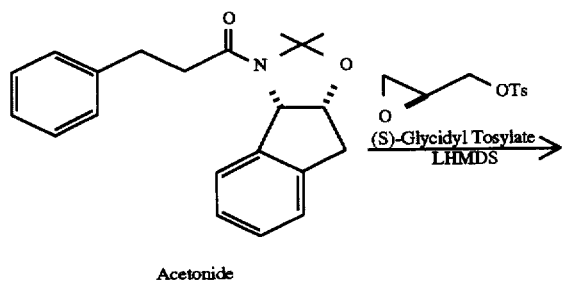

Acetonide

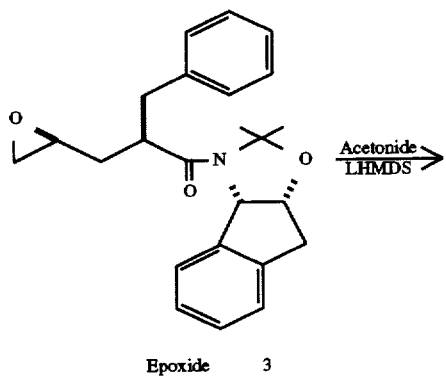

Epoxide 3

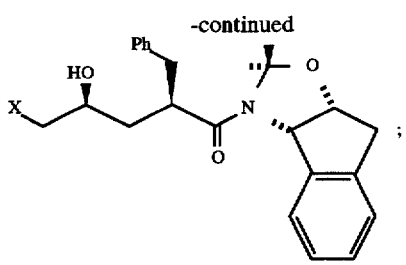

(wherein X is halo)
comprising electrochemical oxidation of the allyl acetonide reactant with halide salt in an aqueous system. The products are useful as intermediates for the synthesis of inhibitors of renin or HIV protease or other proteases.

ABBREVIATIONS

| Designation | |
|---|---|
| A | amperes of current |
| (Boc)₂O (BOC₂O or Boc₂O) | di-t-butyl dicarbonate |
| (+)-CSA | (1S)-(+)-10-camphorsulfonic acid |
| DMF | dimethylformamide |
| Et3N | triethylamine |
| EtOAc | ethyl acetate |
| h | hour(s) |
| IPAC or IPAc | isopropylacetate |
| LHMDS | lithium hexamethyldisilazide |
| MTBE | methyl t-butyl ether |
| THF | tetrahydrofuran |

DETAILED DESCRIPTION OF THE INVENTION

In the present invention, a process is described for the synthesizing the epoxide of formula,

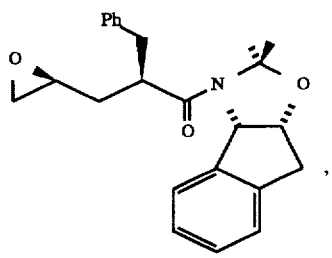

comprising the steps of:
(a) providing a quantity of the allyl acetonide of the structure

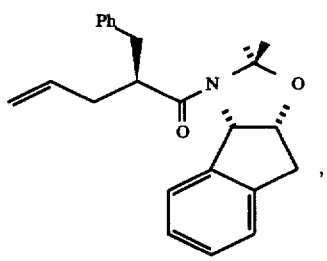

in aqueous mixture with between about 0.2 to about 2.0 equivalents of halide salt, and a water miscible cosolvent;
(b) subjecting said mixture to an electric current density of between about 0.01 A/cm² and about 0.5 A/cm² at a temperature of between about −40° C. and about 100° C.;
(c) to give the desired epoxide.

Another embodiment of the present invention is a process for the synthesizing the halohydrin of formula,

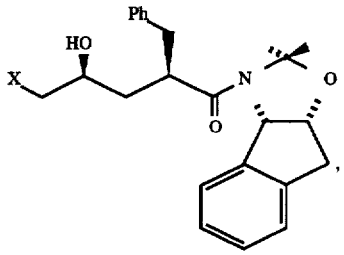

wherein X is halo;
comprising the steps of:
(a) providing a quantity of the allyl acetonide of the structure

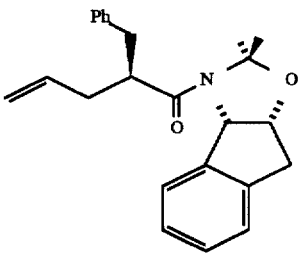

in aqueous mixture with between about 0.2 to about 2.0 equivalents of halide salt, and a water immiscible solvent;
(b) subjecting said mixture to an electric current density of between about 0.01 A/cm² and about 0.5 A/cm² at a temperature of between about −40° C. and about 100° C.;
(c) to give the desired halohydrin.

In the processes of the present invention, halo is preferably either iodide or bromide. The halide salt is preferably selected from the group consisting of NaI, NaBr, KI, KBr, Et₄NI and Et₄NBr. The water miscible cosolvent, when used, is preferably selected from the group consisting of THF, acetonitrile, DMF and NMP (N-methylpyrollidinone), and mixtures thereof. The water immiscible solvent, when used, is preferably selected from the group consisting of ethyl acetate, isopropyl acetate, related esters, toluene, methylene chloride and related halogenated solvents.

In the present invention, the electrochemical process of step (b) is preferably carded out at a current density of about 0.1 A/cm², in an undivided flow cell, at a temperature range between about 0° C. and about 35° C., for a time period to complete the reaction of between about 1 hour and about 10 hours.

More specifically, another embodiment of the present invention is a process for the synthesizing the epoxide of formula,

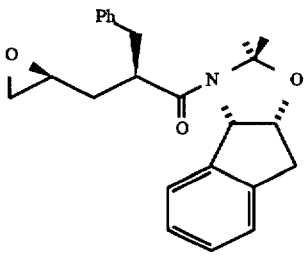

comprising the steps of:

(a) providing one equivalent of the allyl acetonide of the structure

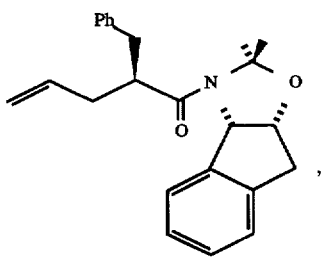

in aqueous suspension with between about 0.2 equivalents and about 2.5 equivalents of NaBr in a mixture of acetonitrile in water;

(b) subjecting said suspension to an electric current density of about 0.1 A/cm$^2$, in an undivided flow cell, at a temperature of about 20° C., for between about 1 hour and about 10 hours;

(c) to give the desired epoxide.

Another embodiment of this invention is the process for synthesizing the halohydrin of formula,

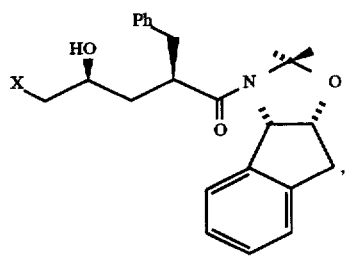

wherein X is chloro or bromo;
comprising the steps of:

(a) providing one equivalent of the allyl acetonide of the structure

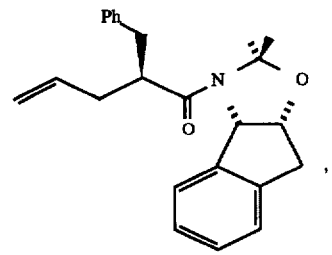

in a biphasic system containing between about 0.2 equivalents and about 2.5 equivalents of NaI or NaBr in ethyl acetate or isopropyl acetate;

(b) subjecting said biphasic system to an electric current density of about 0.1 A/cm$^2$, in an undivided flow cell, at a temperature of about 20° C., for between about 1 hour and about 10 hours;

(c) to give the desired halohydrin.

The present invention may be divided into two processes, one involving the synthesis of epoxide, the other involving synthesis of halohydrin. The two processes are substantially parallel, except for the solvent used during the electrochemical oxidation of step (b). In the epoxide process, a water miscible solvent is employed, whereas for the halohydrin synthesis, a water immiscible solvent is employed.

A. Synthesis of Epoxide

The process for the synthesis of epoxide in the present invention is illustrated by the following Scheme:

SCHEME GAMMA

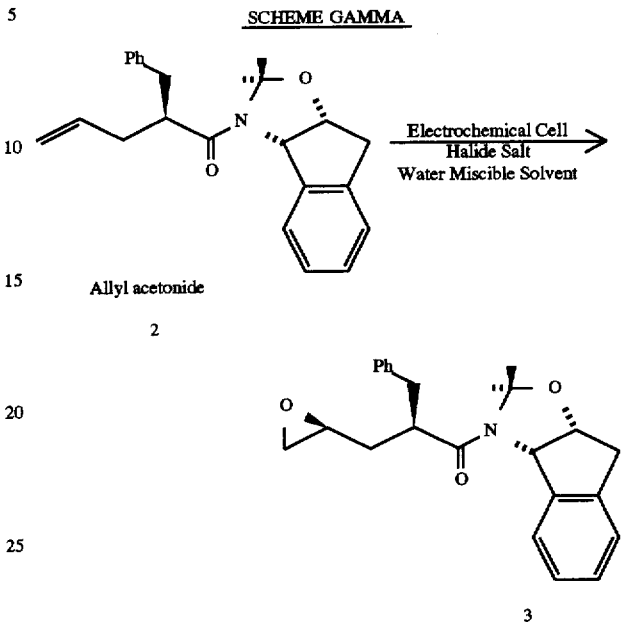

Allyl acetonide

2

3

Reaction conditions for the formation of the epoxide are the use of a divided or undivided electrochemical cell with anodes and cathodes that are stable to the reaction conditions. The anode and cathode materials include, but are not limited to, graphite, palladium, platinum, iridium, nickel, stainless steel, titanium, titanium dioxide or other special makes such as coated titanium dioxide or coated stainless steel. One preferred electrochemical cell is an undivided flow cell.

During the electrochemical process, the current density is maintained between about 0.01 A/cm$^2$ and about 0.5 A/cm$^2$, preferably about 0.1 A/cm$^2$. The choice of current density depends on the type of electrode, its geometry, the geometry of the electrochemical cell and the distance between the anode and cathode. Preferably the current density is kept constant during the reaction. The voltage typically rises during the reaction, but usually stays within a safe range, e.g., about 0.1–10 volts.

Preferred halogenating reagents include halide salts in aqueous system, such as the bromides or iodides of Na, K, Li, Ca, or Mg. Other preferred halide salts include quaternary ammonium salts, such as Et$_4$NBr. Most preferred halide salts are bromides or iodides of Na, K. Quantities of halide salt can vary between about 0.2 to about 2.0 or more equivalents of allyl acetonide 2.

Reaction conditions include solutions, suspensions, or other biphasic systems containing the allyl acetonide reactant, the halogenating reagent and a water miscible solvent. Suitable water miscible solvents include but are not limited to THF, acetonitrile, DMF, or NMP (N-methylpyrrolidinone). One preferred set of reaction conditions for the synthesis of the epoxide is a suspension in a mixture of acetonitrile and water.

Temperature range is between about –40° C. and about 100° C., but preferably between about 0° C. and about 35° C.

The typical time span to complete the reaction is between about 1 hour and about 10 hours. The time needed to complete the reaction depends on the size of the electrodes as well as the geometry of the electrochemical cell.

B. Synthesis of Halohydrin

Alteratively, the electrochemical processes of the present invention are applied to synthesis the stable intermediate halohydrin 3a.

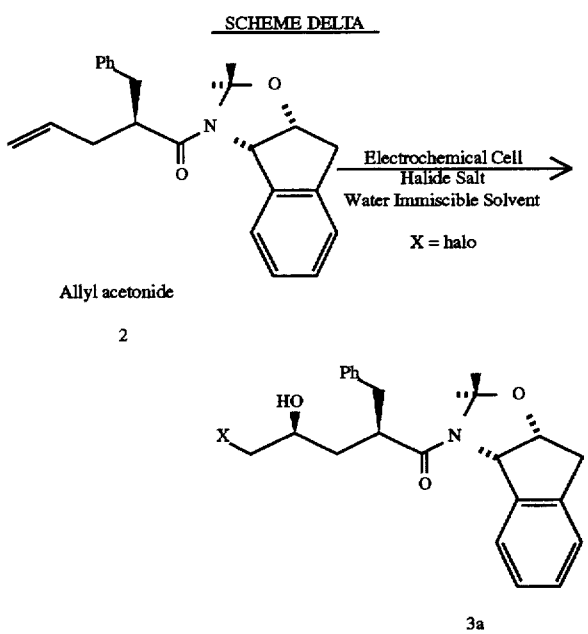

SCHEME DELTA

Allyl acetonide
2

3a

Reaction conditions for the formation of the epoxide are the use of a divided or undivided electrochemical cell with anodes and cathodes that are stable to the reaction conditions. The anode and cathode materials include, but are not limited to, graphite, palladium, platinum, iridium, nickel, stainless steel, titanium, titanium dioxide or other special makes such as coated titanium dioxide or coated stainless steel. One preferred electrochemical cell is an undivided flow cell.

During the electrochemical process, the current density is maintained between about 0.01 A/cm$^2$ and about 0.5 A/cm$^2$, preferably about 0.1 A/cm$^2$. The choice of current density depends on the type of electrode, its geometry, the geometry of the electrochemical cell and the distance between the anode and cathode. Preferably the current density is kept constant during the reaction. The voltage typically rises during the reaction, but usually stays within a safe range, e.g., about 0.1–10 volts.

Preferred halogenating reagents include halide salts in aqueous system, such as the bromides or iodides of Na, K, Li, Ca, or Mg. Other preferred halide salts include quaternary ammonium salts, such as Et$_4$NBr. Most preferred halide salts are bromide or iodides of Na or K. Quantities of halide salt can vary between about 0.2 to about 2.0 or more equivalents to allyl acetonide 2.

Reaction conditions for halohydrin synthesis include solutions, suspensions, or other biphasic systems containing the allyl acetonide reactant, the halogenating reagent and a water immiscible solvent. Suitable water immiscible solvents include but are not limited to ethyl acetate, isopropyl acetate, butylacetate and related esters, as well as toluene, methylene chloride and related halogenated solvents. One preferred set of reaction conditions for the synthesis of the halohydrin 3a is a biphasic system with ethyl acetate and NaI in water.

Temperature range for the synthesis of halohydrin 3a by electrochemical treatment is between about −40° C. and about 100° C., but preferably between about 0° C. and about 35° C.

The typical time span to complete the reaction is between about 1 hour and about 10 hours. The time needed to complete the reaction depends on the size of the electrodes as well as the geometry of the electrochemical cell.

The processes and intermediates of this invention are useful for the preparation of end-product compounds that are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable, e.g., X, occurs more than one time in any constituent, its definition on each occurrence is independent of its definition at every other occurrence. Also, combinations of substituents and/or variables are permissible only if such combinations result in stable compounds.

As used herein except where noted, "Halo" means fluoro, chloro, bromo and iodo.

Representative experimental procedures utilizing the novel process are detailed below. These procedures are exemplary only and should not be construed as being limitations on the novel process of this invention.

EXAMPLE 1

ELECTROCHEMICAL OXIDATION

A. Electrochemical Epoxidation

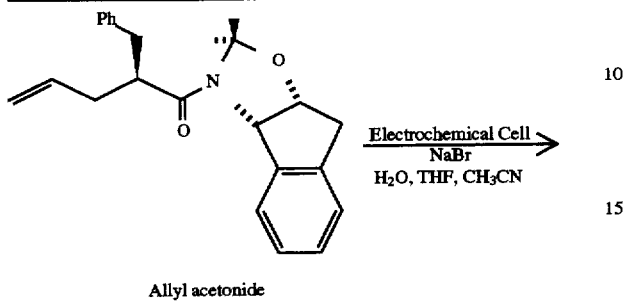

Allyl acetonide

2

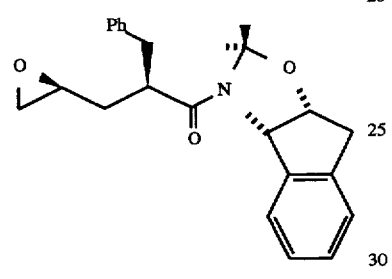

Epoxide

3

| Allyl acetonide | 5.00 g (13.8 mmol) |
| --- | --- |
| Sodium bromide | 2.45 g (24 mmol) |
| H$_2$O | 50 mL |
| CH$_3$CN | 50 mL |
| THF | 20 mL |

The reagents and solvents were combined in a jacketed vessel equipped with a magnetic stirrer and electrodes made from graphite and carbon felt. A constant electrical current of 0.5 A was applied and the vessel was kept at 20° C. After completion of the reaction the organic solvent was evaporated and the product was extracted into MTBE. After aqueous washes the MTBE was evaporated and the residual product was then crytallized from MTBE to give 4.24 g (81%) of the epoxide as a white solid.

B. Electrochemical Formation of Halohydrin

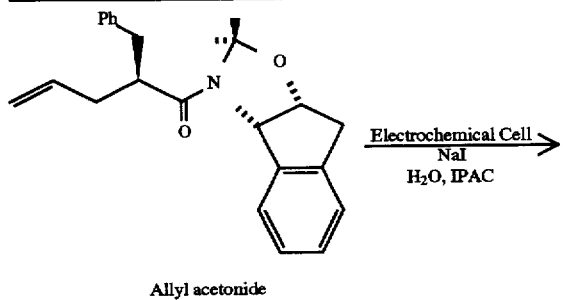

Allyl acetonide

2

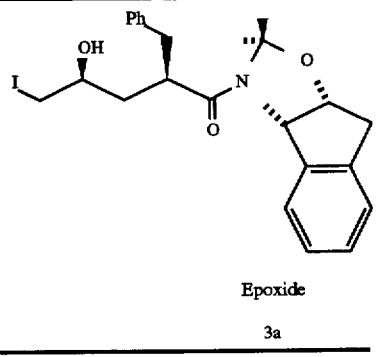

Epoxide

3a

| Allyl acetonide | 5.00 g (13.8 mmol) |
| --- | --- |
| Sodium iodide | (24 mmol) |
| H$_2$O | 50 mL |
| isopropyl acetate | 30 mL |

The reagents and solvents are combined in a jacketed vessel equipped with a magnetic stirrer and electrodes made from graphite and carbon felt. A constant electrical current of 0.5 A is applied and the vessel is kept at 20° C. After completion of the reaction the product 3a is isolated.

EXAMPLE 2

Conversion of Acetonide to Allyl Acetonide

A.

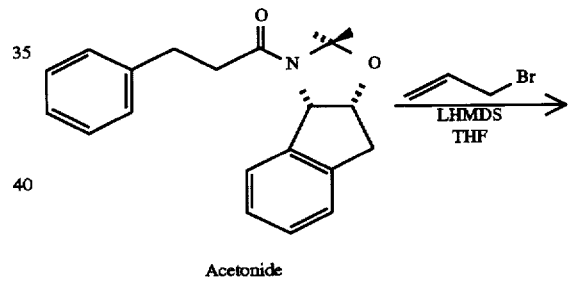

Acetonide

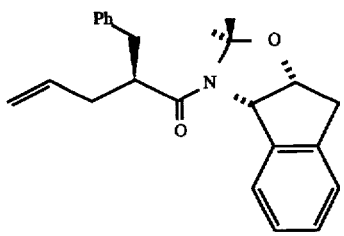

Allyl acetonide 2

| Acetonide | 32.1 g |
| --- | --- |
| Allyl bromide | 12.70 g |
| Lithiumhexamethyldisilazide (LHMDS) 1.0M in THF | 105 mL |
| Tetrahydrofuran (THF) | 200 mL |

The acetonide was dissolved in 200 mL THF in a 100 mL 3 neck flask equipped with an addition funnel and degassed by bubbling in nitrogen for 20 min. The mixture was cooled to −25° C. and the allyl bromide was added via a weighed syringe. The LHMDS was transferred to the addition funnel under nitrogen pressure via cannula. The LHMDS was allowed to slowly drop into the magnetically stirred reaction mixture over 20 min. The interval temperature reached −14° C. while the cooling bath was at −30° C. The mixture was aged at −20° to −15° C. for 30 min. Water (100 mL) and IPAC (100 mL) were added and the temperature rose to 5° C. The lower aqueous phase was discarded and the organic phase was washed with 100 mL of 0.2M HCl in 3% aq. NaCl, 30 mL brine, and 30 mL 0.5M sodium bicarbonate. The organic phase was evaporated (55° C., 100 Torr) to an oil, another 40 mL of IPAC were added, and the mixture was again evaporated to an oil. At this point the crude allyl acetonide may be taken directly on to the next step or purified by crystallization from 30:1 hexane-IPAC or 30:1 methylcyclohexane-IPAC to give the allyl acetonide as a white crystalline solid in 87% yield.

| Allyl acetonide $^{13}$C NMR data for major rotamer (62.5 MHz) | | | |
|---|---|---|---|
| 171.0 | 140.4 | 140.2 | 134.8 |
| 129.6 | 128.6 | 128.2 | 127.1 |
| 126.6 | 125.6 | 124.0 | 117.9 |
| 96.8 | 78.9 | | |
| | 65.6 | 47.5 | 38.6 |
| 38.0 | 36.1 | 26.6 | 24.1 ppm |

B. Synthesis of Allyl Acetonide

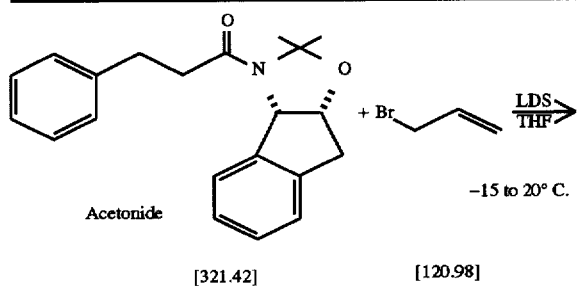

Allyl Acetonide

[361.49]

| Acetonide | | 200 g | | 0.617 mol |
|---|---|---|---|---|
| Allyl Bromide | | 77.6 g | 53.6 mL | 0.642 mol |
| LDS | 1.32M in THF | | 518 mL | 0.684 mol |
| Citric acid | | 35.73 g | | 0.186 mol |
| THF sieve dried | 1.43 L | | | |
| Water | 1.05 L | | | |
| 0.3M H$_2$SO$_4$ | 1.18 L | | | |
| 6% NaHCO$_3$ | 1.18 L | | | |
| IPAc | | | | |

The crystalline acetonide (200 g, 0.622 mol, 99.1 wt. %) is dissolved in 1.25 L sieve dried THF (KF=11 mg/L) under nitrogen atmosphere at 25° C. with mechanical stirring. The resulting KF of the solution at this point is 40 mg/L. The solution is subjected to three alternating vacuum/nitrogen purge cycles to thoroughly degas the solution of dissolved oxygen.

Allyl bromide is added to the THF solution. The resulting KF was 75 mg/L. Typical complete conversion (>99.5%) has been obtained with pre-LDS solution KF levels of 200 mg/L with the 10% base excess present. The solution was then cooled to −20° C. A THF solution of lithium hexamethyldisilazide (LDS, 1.32M) is added to the allyl bromide/3 solution at such a rate as to maintain the reaction temperature at −20° C. The LDS addition took 30 min. The mixture was aged at −15° to −20° C. and quenched when the conversion was >99%. Analysis of the reaction was carried out by HPLC. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°-15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by $^1$H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86 L.

The pH of the mixture after the three aqueous washes was 6.5, 1.3 and 8.5, respectively. HPLC analysis of the mixture at this point indicated 93–94 % assay yield for acetonide. The ratio of allyl-acetonide/epi-allylacetonide was 96:4 by HPLC (same conditions as above). GC analysis at this point indicated that the hexamethyldisilazane by-product had been completely removed in the workup.

EXAMPLE 3

Preparation of Amide 1

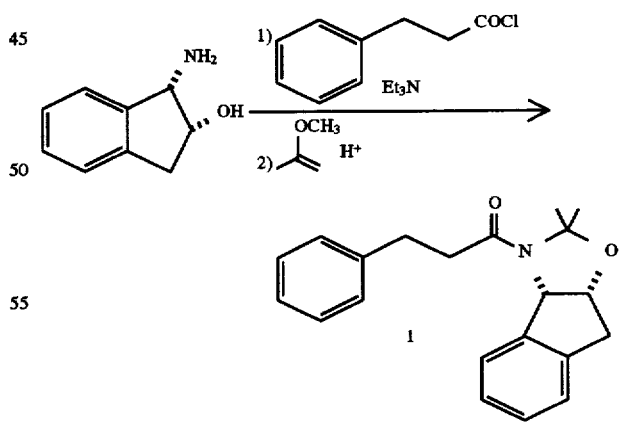

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

| retention time (min.) | identity |
| --- | --- |
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h.

EXAMPLE 4

Preparation of penultimate 6

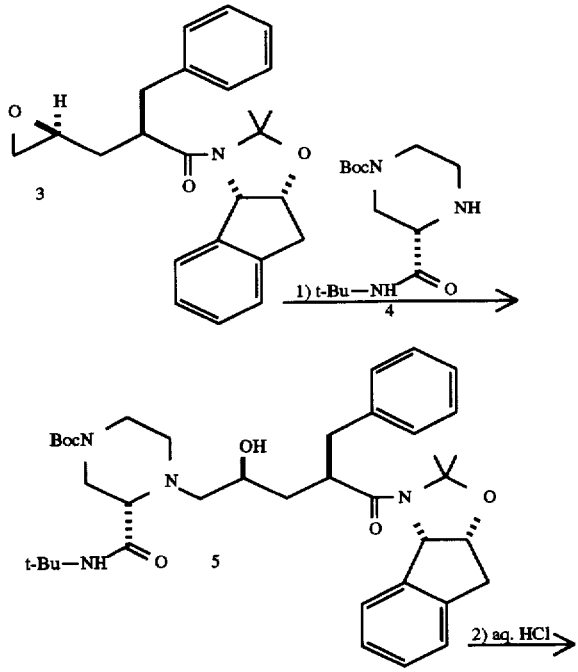

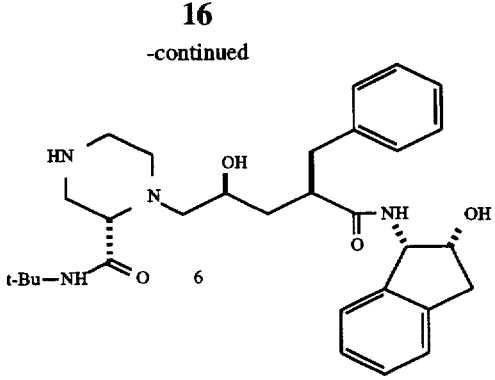

A slurry of the 2(S)-t-butylcarboxamide-4-N-Boc-piperazine 4 (1950 g, 6.83 mol,>99.5% ee) (ee= enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (interval temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM ($KH_2PO_4$/$K_2HPO_4$), 1.0 mL/min., detection=220 nm, sample preparation=2 µL, reaction mixture diluted to 1 mL in acetonitrile. Approximate retention times:

| retention time (min) | identity |
| --- | --- |
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
| --- | --- |
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl$_3$) δ 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 5

Preparation of monohydrate of Compound J

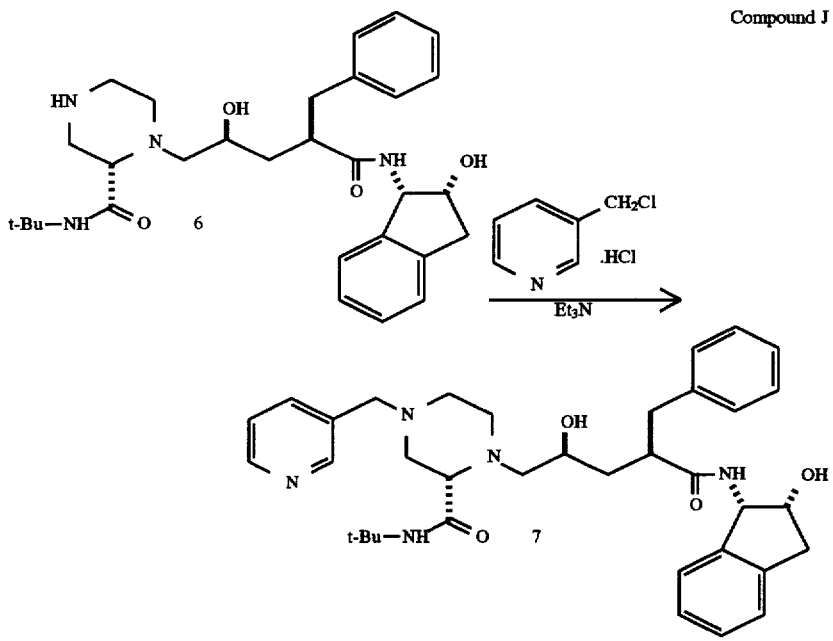

The solution of 6 in DMF (10.5 L, KF=10 mg/mL) from the previous step was charged with 8 L of sieve dried DMF (KF.<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydro chloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 6 |

The mixture was aged at 68° C. until the residual penultimate compound 6 was<0.3 area % by HPLC analysis.

The mixture was stirred at 68° C. for 4 h, then cooled to 25° C. and partitioned with ethyl acetate (80 L) and a mixture of 24 L of saturated aqueous NaHCO$_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 6

Pyrazine-2-tert-butyl carboxamide 9

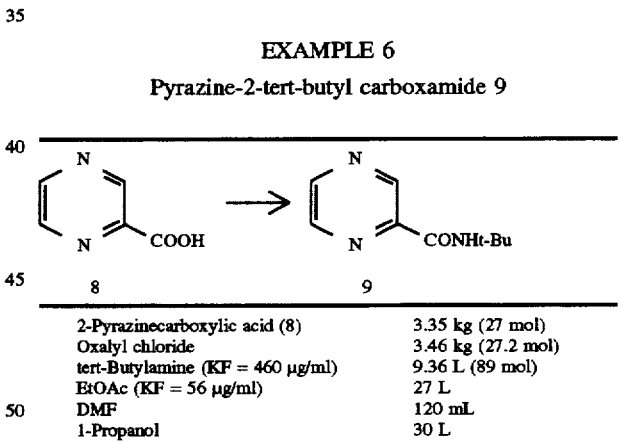

| | |
|---|---|
| 2-Pyrazinecarboxylic acid (8) | 3.35 kg (27 mol) |
| Oxalyl chloride | 3.46 kg (27.2 mol) |
| tert-Butylamine (KF = 460 µg/ml) | 9.36 L (89 mol) |
| EtOAc (KF = 56 µg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under N$_2$ and the suspension was cooled to 2° C. The oxalyl chloride was added, maintaining the temperature between 5° and 8° C.

The addition was completed in 5 h. During the exothermic addition CO and CO$_2$ were evolved. The HCl that was formed remained largely in solution. A precipitate was present which is probably the HCL salt of the pyrazine acid chloride. Assay of the acid chloride formation was carded out by quenching an anhydrous sample of the reaction with t-butylamine. At completion<0.7% of acid 8 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The interval temperature in this solvent change was<30° C. A 1-propanol/EtOAC solution of 3 was stable to reflux atmospheric pressure for several days.

Evaporation of an aliquot gave a tan solid m.p 87°–88° C. $^{13}C$ NMR (75 MHz, $CDCl_3$, ppm) 161.8, 146.8, 145.0, 143.8, 142.1, 51.0, 28.5.

EXAMPLE 7 rac-2-tert-Butylcarboxamide-piperazine 10

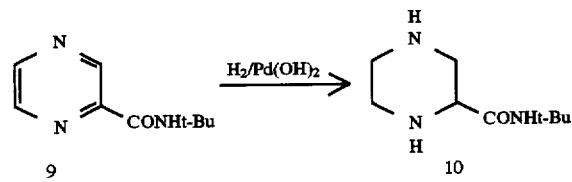

Materials

Pyrazine-2-tert-butylcarboxamide 9 2.4 kg (13.4 mol) in 1-propanal solution 12 L 20% $Pd(OH)_2/C$ 16 wt.% water 144 g The pyrazine-2-tert-butylcarboxamide 9/1-propanol solution was placed into the 5 gal autoclave. The catalyst was added and the mixture was hydrogenated at 65° C. at 40 psi (3 atm) of $H_2$.

After 24 h, the reaction had taken up the theoretical amount of hydrogen and GC indicated<1% of 9. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; $^{13}C$ NMR (75 MHz, $D_2O$, ppm) 173.5, 59.8, 52.0, 48.7, 45.0, 44.8, 28.7.

EXAMPLE 8

(S)-2-tert-Butyl-carboxamide-piperazine bis (S)-Camphorsulfonic acid salt (S)-11

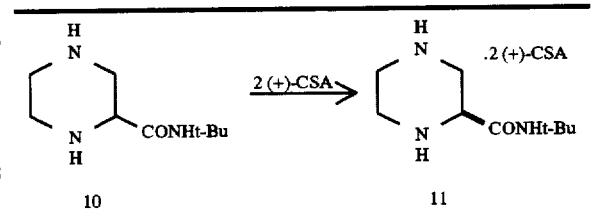

Materials

| | |
|---|---|
| rac-2-tert-Butyl-carboxamide-piperazine 10 in 1-propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature<25° C. to a volume of ca 12 L.

At this point the product had precipitated from the solution, but went back into a solution when the mixture was heated to 50° C.

Analysis of a homogeneous aliquot indicated that the concentration of 10 was 341 g/L The concentration was determined by HPLC: 25 cm Dupont Zorbax RXC8 column with 1.5 mL/min flow and detection at 210 nm, isocratic (98/2) $CH_3CN/0.1$% aqueous $H_3PO_4$. Retention time of 10:2.5 min.

Acetonitrile (39 L) and water (2.4 L) were added to give a clear, slightly brown solution.

Determination of the water content by KF titration and $CH_3CN$/1-propanol ratio by $^1H$ NMR integration showed that the CH3CN/1-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21 ° C. over 8 h.

The product precipitated at 62° C. The product was filtered without aging at 21° C., and the filter cake was washed with 5 L of the $CH_3CN$/1-propanol/$H_2O$ 26/8/1.6 solvent mixture. It was dried at 35° C. in the vacuum oven with $N_2$ bleed to give 5.6 Kg (39%) of 11 as a white crystalline solid m.p 288°–290° C. (with decomp.) $[\alpha]D^{25}=$ 18.9° (c=0.37, H₂O). ¹³C NMR (75 MHz, D₂O, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of Et₃N. Boc₂O (11 mg) was added and the reaction mixture was allowed to age for 1h. The solvent was completely removed in vacuo, and the residue was dissolved in ca. 1 mL of EtOAc and filtered through a Pasteur pipet with SiO₂, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 9

(S)-2-tert-Butylcarboxamide-4-tert-butoxycarbonyl-piperazine 4 from salt 11

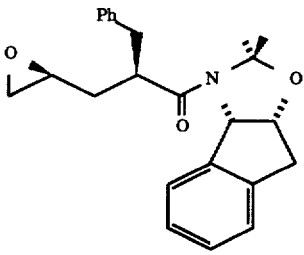

Materials

| (S)-2-tert-Butyl-carboxamide-piperazine Bis (S)-(+)-CSA salt 11, 95% ee | 5.54 Kg (8.53 mol) |
| --- | --- |
| Di-tert-butyl dicarbonate | 1.86 Kg (8.53 mol) |
| Et₃N | 5.95 L (42.6 mol) |
| EtOH Punctilious 200 proof | 55 L |
| EtOAc | 2 L |

To the (S)-CSA salt 11 in a 100 L 3-neck flask with an addition funnel under N2 was added EtOH, followed by triethylamine at 25° C. The solid dissolved readily on the addition of the Et₃N. The Boc₂O was dissolved in EtOAc and charged to the addition funnel. The solution of Boc₂O in EtOAc was added at such a rate as to keep the temperature below 25° C. The addition took 3 h. The reaction mixture was aged for 1 h after completion of the addition of the Boc₂O solution.

The reaction can be monitored by HPLC:25 cm Dupont Zorbax RXC8 column with 1 mL/min flow and detection at 228 nm. isocratic (50/50) CH₃CN/0.1M KH₂PO₄ adjusted to pH=6.8 with NaOH. Retention time of 4=7.2 min. The chiral assay was carried out using the same system as in the previous step. The reaction could also be monitored by TLC with a 100% EtOAc as the solvent. (R_f=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous Na₂CO₃ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an interval temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under N₂ bleed to give 1.87 Kg (77%,>99.9 area % by HPLC, R-isomer below level of detection) of 4 as a slightly tan powder. [α]D²⁵=22.0° (c=0.20, MeOH), m.p 107° C.; ¹³C NMR (75 MHz, CDCl₃, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and it equivalents.

What is claimed is:

1. A process for synthesizing an epoxide of formula,

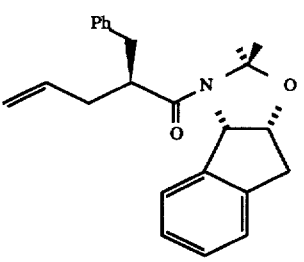

comprising the steps of:

(a) providing a quantity of allyl acetonide having a structure in aqueous mixture with between about 0.2 to about 2.0 equivalents of halide salt, and a water miscible cosolvent;

(b) subjecting said mixture to an electric current density of between about 0.01 A/cm² and about 0.5 A/cm² at a temperature of between about −40° C. and about 100° C.;

(c) to give the desired epoxide.

2. The process of claim 1 wherein the halide salt is selected from the group consisting of NaI, NaBr, KI, KBr, Et₄NI and Et₄NBr.

3. The process of claim 1 wherein the water miscible cosolvent is selected from the group consisting of tetrahydrofuran, acetonitrile, dimethylformamide and N-methylpyrrolidinone, and mixtures thereof.

4. The process of claim 6 wherein the water immiscible solvent is selected from the group consisting of ethyl acetate, isopropyl acetate, related esters, toluene, methylene chloride and related halogenated solvents.

5. The process of claim 1 wherein step (b) is carried out at a current density of about 0.1 A/cm², in an undivided flow cell, at a temperature range between about 0° C. and about 35° C., for a time period to complete the reaction of between about 1 hour and about 10 hours.

6. A process for synthesizing a halohydrin of formula,

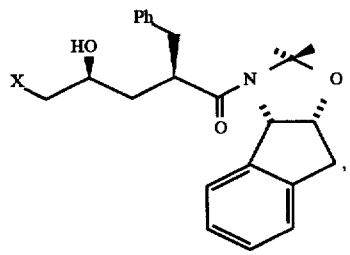

wherein X is halo;

comprising the steps of:

(a) providing a quantity of allyl acetonide having a structure

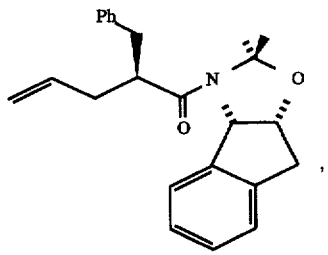

in aqueous mixture with between about 0.2 to about 2.0 equivalents of halide salt, and a water immiscible solvent;

(b) subjecting said mixture to an electric current density of between about 0.01 A/cm² and about 0.5 A/cm² at a temperature of between about −40° C. and about 100° C.;

(c) to give the desired halohydrin.

7. The process of claim 6 wherein halo is either iodide or bromide.

8. The process of claim 7 wherein the halide salt is selected from the group consisting of NaI, NaBr, KI, KBr, Et₄NI and Et₄NBr.

9. The process of claim 7 wherein the water immiscible solvent is selected from the group consisting of ethyl acetate, isopropyl acetate, related esters, toluene, methylene chloride and related halogenated solvents.

10. The process of claim 7 wherein step (b) is carried out at a current density of about 0.1 A/cm², in an undivided flow cell, at a temperature range between about 0° C. and about 35° C., for a time period to complete the reaction of between about 1 hour and about 10 hours.

11. The process of claim 6 wherein the halide salt is selected from the group consisting of NaI, NaBr, KI, KBr, Et₄NI and Et₄NBr.

12. The process of claim 6 wherein step (b) is carried out at a current density of about 0.1 A/cm², in an undivided flow cell, at a temperature range between about 0° C. and about 35° C., for a time period to complete the reaction of between about 1 hour and about 10 hours.

13. A process for synthesizing an epoxide of formula,

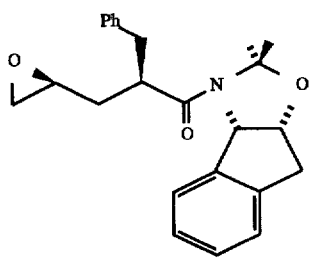

comprising the steps of:

(a) providing one equivalent of allyl acetonide having a structure

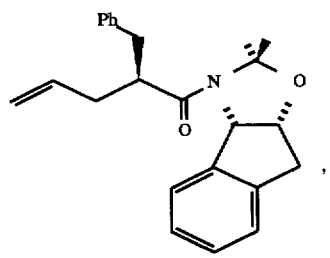

in aqueous suspension with between about 0.2 equivalents and about 2.5 equivalents of NaBr in a mixture of acetonitrile in water;

(b) subjecting said suspension to an electric current density of about 0.1 A/cm², in an undivided flow cell, at a temperature of about 20° C., for between about 1 hour and about 10 hours;

(c) to give the desired epoxide.

14. A process for synthesizing a halohydrin of formula,

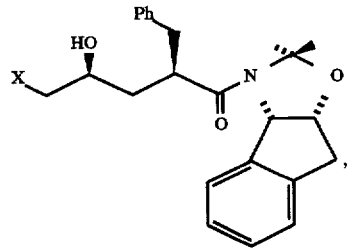

wherein X is chloro or bromo;

comprising the steps of:

(a) providing one equivalent of allyl acetonide having a structure

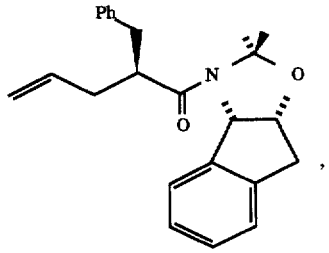

in a biphasic system containing between about 0.2 equivalents and about 2.5 equivalents of NaI or NaBr in ethyl acetate or isopropyl acetate;

(b) subjecting said biphasic system to an electric current density of about 0.1 A/cm$^2$, in an tin divided flow cell, at a temperature of about 20° C., for between about 1 hour and about 10 hours;

(c) to give the desired halohydrin.

* * * * *